(12) United States Patent
Brooks

(10) Patent No.: US 8,685,454 B2
(45) Date of Patent: Apr. 1, 2014

(54) LUBRICATING COMPOSITION

(75) Inventor: Sarah Annabelle Brooks, Petersfield (GB)

(73) Assignee: Yes Syzygy Limited, Hampshire (GB)

( * ) Notice: Subject to any disclaimer, the term of this patent is extended or adjusted under 35 U.S.C. 154(b) by 946 days.

(21) Appl. No.: 11/899,142

(22) Filed: Sep. 4, 2007

(65) Prior Publication Data

US 2008/0146472 A1  Jun. 19, 2008

Related U.S. Application Data

(63) Continuation of application No. PCT/GB2006/000710, filed on Feb. 28, 2006.

(30) Foreign Application Priority Data

Mar. 1, 2005 (GB) .................................. 0504153.8

(51) Int. Cl.
| | | |
|---|---|---|
| *A61K 8/06* | (2006.01) | |
| *A61K 8/18* | (2006.01) | |
| *A61K 8/60* | (2006.01) | |
| *A61K 8/73* | (2006.01) | |
| *A61K 8/97* | (2006.01) | |

(52) U.S. Cl.
USPC .......................................... 424/485; 424/488

(58) Field of Classification Search
USPC .......... 508/216; 424/195.18, 194.18, 65, 101, 424/937, 944, 946, 966, 967, 841, 843, 485, 424/488; 514/937, 944, 946, 966, 967, 841, 514/843

See application file for complete search history.

(56) References Cited

U.S. PATENT DOCUMENTS

| 6,124,248 | A * | 9/2000 | O'Bryant et al. ............. 508/216 |
|---|---|---|---|
| 6,302,208 | B1 * | 10/2001 | Walker et al. ................. 166/278 |
| 6,528,070 | B1 * | 3/2003 | Bratescu et al. .............. 424/401 |
| 6,552,024 | B1 * | 4/2003 | Chen et al. ................ 514/252.16 |
| 6,881,427 | B2 * | 4/2005 | Mayne et al. .................. 424/757 |
| 2003/0150069 | A1 * | 8/2003 | Kleen et al. ......................... 8/561 |
| 2004/0018250 | A1 * | 1/2004 | Ceccoli et al. ................. 424/725 |
| 2004/0131645 | A1 * | 7/2004 | Williams et al. .............. 424/400 |

FOREIGN PATENT DOCUMENTS

| EP | 511181 A1 | * 10/1992 |
|---|---|---|
| WO | WO09316707 | * 9/1993 |

* cited by examiner

*Primary Examiner* — Pamela H Weiss
(74) *Attorney, Agent, or Firm* — Bay State IP, LLC

(57) ABSTRACT

A lubricating composition prepared primarily from organic materials (primarily plants and micro-organisms). The unique process and mixture of organic materials comprising this lotion provide with superior properties for various uses. The lotion exists as a viscous liquid with mucosa moistening properties. Some suggested applications for the lotion are that it may be used as a means for delivering medication, skin moisturizing and to enhances sexual experiences.

17 Claims, No Drawings

LUBRICATING COMPOSITION

This application is a continuation of and claims the benefit of International Application No. PCT/GB2006/000710 having an international filing date of Feb. 28, 2006 under 35 U.S.C. §120, and which in turn claims priority to U.K. Patent Application No. 0504153.8 filed on Mar. 1, 2005.

The present invention relates to a lubricating composition, particularly though not exclusively for use in love making.

Lubricating gels are known. Generally they comprise synthetic lubricating agents such as glycerine, propylene glycol, hydroxyethyl cellulose, etc.

It is known from EP 0511181 A1 to use linseed polysaccharide aqueous extract as a saliva substitute in dry mouth condition, i.e. xerostomia.

The object of the present invention is to provide a lubricating composition prepared primarily from organic—here meaning plant and/or micro-organism based/nature-identical matter—components.

According to the invention there is provided a lubricating composition comprising a seed polysaccharide aqueous extract.

In this specification, a polysaccharide aqueous extract is also referred to as a gum.

I prefer to use linseed (flax) seed extract, because varying its concentration in the composition is a convenient means of controlling the viscosity of the composition and because of its muco-adhesion properties. It can be present as a dry weight percentage between 0.001% and 10%.

This extract is a viscous liquid obtained by an aqueous extraction of the seeds of the linseed plant, before or after pressing for extraction of oil. The raw extract has a viscosity of 50-500 cPs or higher depending on water-to-linseed ratio.

In preferred compositions, an additional component is at least one further polysaccharide aqueous extract, for instance Xanthan gum, Yellow Mustard seed gum, Acacia gum, gums from seaweeds (eg Alginates or Carrageenan), β-Glucans (derived from barley, oats, rye and wheat) and fruit gums. Preferred additional gums are Galactomannan gums, since they exhibit a synergistic phenomena resulting from their Galactomannan structures of long smooth sections of their molecules, for example Locust Bean gum, Guar gum, Cassia gum, Tara Gum, and Konjac Mannan gel which is a Glucomannan and is stereochemically similar to a Galactomannan. Certain of these gums are prepared in the manner of the linseed extract, for instance Yellow Mustard seed gum. Xanthan gum is prepared by action of the *Xanthomonas campestris* on maize seed. Typically these gums can be present as a dry weight percentage between 0.001% and 5%.

These further polysaccharide aqueous extracts also are viscous liquids.

There is a synergistic effect in the combination of two gums, for instance linseed gum and Xanthan gum, in that the viscosity of the combined gums is higher than the average viscosity of the individual gums. This effect is particularly marked where the gums both have smooth Galactomannan regions.

The preferred viscosity for the lubricating composition is between 100 and 15,000 cPs. This is higher than the viscosity of the raw linseed extract and is achieved by the addition of a relatively low concentration of Xanthan gum. However, it should be noted that viscosity as conventionally measured is not the only advantageous property. Its rheological properties of shear thinning are also important.

Preferably, the lubricating composition includes at least one preservative for prevention of growth of micro-organisms and preserving stability of the composition. For control of fungi, moulds and bacteria it is preferred to provide more than one preservative. Where possible I prefer to use plant based/nature-identical preservatives e.g. Potassium Sorbate (found in citrus fruit), grapefruit seed extract (Citricidal), for control of moulds and fingi; I found it necessary to use a synthetic preservative for control of bacteria, for example phenoxyethanol.

The composition is preferably pH buffered to be compatible with mucous membranes of the human body. The preferred buffer is Citric Acid. The composition can have a pH of between 4.0 and 6.0. Preferably it is between 4.5 and 5.5.

The linseed gum can include a small quantity of linseed oil. Where this is the case, an antioxidant such as Vitamin E is preferably included in the composition.

The composition can be formulated as a gel or as a lotion or cream or as a solid.

Again, the composition can be an emulsion typically with a plant oil or a vegetable butter or beeswax. Such emulsion will usually include an emulsifying agent, such as lecithin. Examples of suitable plant oils are sunflower, canola, safflower, avocado and pomegranate oil. Examples of suitable vegetable butters are shea and cocoa butter.

A herbal extract can be added, for instance aloe vera.

According to a second aspect of the invention there is provided a composition for application to mucous membranes of the human body (the mucosa) comprising a seed polysaccharide aqueous extract in combination with a medicament for treating the mucosa.

To help understanding of the invention, an example of a lubricating composition will now be described.

Linseed is mixed with water in a ratio of 1 part linseed to 10 parts water. It is heated to 80° C. and held for 30 minutes. The solid material is separated off by filtration.

The filtrate contains linseed polysaccharide gum. 0.5% by weight of potassium sorbate, 0.1% by weight of Vitamin E (Tocopherol), and sufficient citric acid (a small quantity) is added to achieve pH 5. This still low viscosity composition is mixed with a 1% by weight solution of Xanthan gum at ambient temperature. The resultant composition is a thick gel, typically having a desired 12,000 cPs viscosity. It is thixotropic and pseudoplastic. Linseed gum is known to adhere to human mucous membranes and is known to be cytoprotective. Further it is non-toxic and non-irritant. These properties render it suitable for use in a personal lubricant.

It is bottled in so called bottles, i.e. invert bottles from which the composition can be squeezed for use from below, lowering exposure of the composition to contamination. Dispensing in this way enables the use of preservative to be held low.

Both liquid and solid emulsions are prepared by similar methods. The water phase (polysaccharide aqueous mixture as described above) is added to the oil phase; a mixture of warmed oils, bees wax and butters (e.g. sunflower oil, Cocoa or Shea butters). The bees wax and butters are melted by the warming to ensure mixing is complete. Both phases as placed in a vessel with a shear mixer/emulsifier. The shear mixer is turned on and an emulsifying agent, preferably Lecithin, is added slowly until the desired emulsion is obtained. For a solid emulsion (at 21° C.) higher quantities of bees wax and butters are added and a much reduced amount of the water phase is included. For a liquid emulsion less bees wax and butters are added and greater amounts of the water phase are added, this also requires slightly more of the emulsifying agent to be added. Exact proportions are determined by the desired end result.

The invention is not intended to be restricted to the details of the above described embodiment. For instance, the linseed gum can be purified by alcoholic precipitation.

Further it is envisaged that the composition can be used as a vehicle for delivering medication either in a lubrication environment or a prophylactic environment. Envisaged medication includes and is not restricted to anti-thrush (*Candida albicans*) medication. Furthermore, the composition has mucosa moisturizing properties on its own.

What is claimed is:

1. A personal lubricating composition of an aqueous viscous gel comprising:
   a water soluble polysaccharide gum, wherein the gum is extracted from linseed;
   a second polysaccharide gum, wherein the polysaccharide gum is soluble in water and wherein the second polysaccharide gum is selected from the group consisting of Galactomannan gums and Xanthan gum;
   a pH buffer;
   at least one preservative, wherein the preservative is for the prevention of micro-organisms and the stability of the composition; and
   wherein the combination of polysaccharide gums is for use as an aqueous viscous gel mucous membrane lubricant and to provide an increase in the consistency of viscosity of the lubricating composition over the variable viscosity of individual linseed gum extracts.

2. The personal lubricating composition of an aqueous viscous gel of claim 1, wherein the pH buffer is between 4.00 and 6.00.

3. The personal lubricating composition of an aqueous viscous gel of claim 2, wherein the pH buffer is between 4.50 and 5.50.

4. The personal lubricating composition of an aqueous viscous gel of claim 1, wherein the pH buffer is citric acid.

5. The personal lubricating composition of an aqueous viscous gel of claim 1, wherein the water soluble polysaccharide gum extracted from linseed is present as a dry weight percentage between 0.001% and 10.00%.

6. The personal lubricating composition of an aqueous viscous gel of claim 1, wherein the Galactomannan gum is selected from the group consisting of Locust Bean gum, Guar gum, Casia gum, and Tara gum.

7. The personal lubricating composition of an aqueous viscous gel of claim 6, wherein the Galactomannan gum is present as a dry weight percentage between 0.001% and 5.00%.

8. The personal lubricating composition of an aqueous viscous gel of claim 1, wherein the Xanthan gum is present as a dry weight percentage between 0.0001% and 5.00%.

9. The personal lubricating composition of an aqueous viscous gel of claim 1, wherein the composition possesses a viscosity of between 100 and 15,000 cP's.

10. The personal lubricating composition of an aqueous viscous gel of claim 1, wherein the preservative is selected from the group consisting of potassium sorbate and phenoxyethanol.

11. The personal lubricating of an aqueous viscous gel composition of claim 1, wherein the composition further comprises an antioxidant.

12. The personal lubricating composition of an aqueous viscous gel of claim 11, wherein the antioxidant is Vitamin E.

13. The personal lubricating composition of an aqueous viscous gel of claim 1, wherein the formulation of the composition is an aqueous viscous gel, and wherein the gel is utilized as an aqueous phase selected from the group consisting of a lotion, a cream, and an emulsion.

14. The personal lubricating composition of an aqueous viscous gel of claim 13, wherein the personal lubricating composition comprises an emulsion comprising a hydrophobic portion which comprises a quantity of material selected from the group consisting of plant oil, vegetable butter, and beeswax.

15. The personal lubricating composition of an aqueous viscous gel of claim 14, wherein the resultant emulsion further comprises an emulsifying agent.

16. The personal lubricating composition of an aqueous viscous gel of claim 1, wherein the composition further comprises a herbal extract.

17. The personal lubricating composition of an aqueous viscous gel of claim 1, wherein the composition is in a liquid state and contained within a tottle.

* * * * *